United States Patent [19]

Bach et al.

[11] Patent Number: 4,500,545

[45] Date of Patent: Feb. 19, 1985

[54] HYDROXYAMINOTETRALINCARBOXA-MIDES

[75] Inventors: Nicholas J. Bach; Edmund C. Kornfeld; Robert D. Titus, all of Indianapolis, Ind.

[73] Assignee: Eli Lilly and Company, Indianapolis, Ind.

[21] Appl. No.: 588,180

[22] Filed: Mar. 12, 1984

Related U.S. Application Data

[62] Division of Ser. No. 442,074, Nov. 16, 1982, Pat. No. 4,448,990.

[51] Int. Cl.³ ............................................. A61K 31/165
[52] U.S. Cl. ..................................................... 514/619
[58] Field of Search ......................................... 424/324

[56] References Cited

U.S. PATENT DOCUMENTS 4,410,519 10/1983 Seiler et al. ........................ 424/226

FOREIGN PATENT DOCUMENTS 1597140 9/1981 United Kingdom .

OTHER PUBLICATIONS

Long et al., J. Pharmacology & Exp. Therapeutics, vol. 192, No. 2, pp. 330–342.
J. Med. Chem., vol. 24, No. 10, 10/81.
Science, vol. 210, 12/80, pp. 1141–1143.

*Primary Examiner*—Stanley J. Friedman
*Attorney, Agent, or Firm*—James L. Rowe; Arthur R. Whale

[57] ABSTRACT o-Hydroxy tetralin carboxamides, substituted with an amino group in the aliphatic ring, are dopamine agonists.

12 Claims, No Drawings

HYDROXYAMINOTETRALINCARBOXAMIDES

This application is a division of application Ser. No. 442,074, filed Nov. 16, 1982, now U.S. Pat. No. 4,448,990.

BACKGROUND OF THE INVENTION

Aminotetralins which have dopamine-like pharmacological activity are known. For example, Woodruff, *Comp. Gen. Pharmacol.*, 2, 439 (1971) describes 2-amino-6,7-dihydroxy-1,2,3,4-tetralin (ADTN) and states that it has a dopamine-like action. M7(2-dimethylamino-5,6-dihydroxy-1,2,3,4-tetralin) is also said to have dopamine-like activity—see Cannon et al., *J. Med. Chem.*, 15, 348 (1972) and Long et al. *J. Pharm. Exper. Therap.*, 192, 336 (1975). Its action parallels that of apomorphine. The 6,7-dihydroxy isomer is also said to be a presynaptic dopamine receptor agonist, according to Lander et al., *Science*, 210, 1141 (1980).

Derivatives of 5-hydroxy-6-methyl-2-amino-1,2,3,4-tetralin are disclosed in Cannon et al., *J. Med. Chem.*, 23, 750 (1980). Cannon et al., ibid, 24, 1113 (1981) review the chemistry and pharmacological activity of aminohydroxytetralins.

Belgian Pat. No. 861,516 and West German Pat. No. 2,803,582 disclose 1-mesylamido-2-hydroxy-6-amino (or dialkylamino)-5,6,7,8-tetrahydronaphthalene and 2-mesylamido-3-hydroxy-7-amino (or dialkylamino)-5,6,7,8-tetrahydronaphthalene, both said to be dopamine-like compounds.

Japanese researchers at Takeda have disclosed 1-hydroxymethyl-2,5-dihydroxy-6-isopropylamino-5,6,7,8-tetrahydronaphthalene, and have stated that it is a bronchodilator—see *Arzneim. Forsch./Drug. Res.*, 30, 276 (1980).

In related pharmacological areas, U.S. Pat. No. 4,101,677 claims 1-alkylamino (or dialkylamino)-1,2,3,4-tetralins, useful in inducing anesthesia; and U.S. Pat. No. 4,320,148 describes 5 and 8-substituted-2-amino-1,2,3,4-tetralins with central α-agonist action where the substituents are methoxy, methylthio, ethylthio, phenylthio and trifluoromethylthio.

The above references are not cited as a complete review of the voluminous aminohydroxytetralin literature, but do include publications describing dopamine-like compounds with those structural characteristics plus a few other recent patents in the general field.

A search of the chemical literature has uncovered no carboxamido-substituted hydroxyaminotetralins, such as are disclosed and claimed herein.

DESCRIPTION OF THE INVENTION

This invention provides carboxamido-substituted hydroxyaminotetralins (or tetrahydronaphthalenes) of the formula

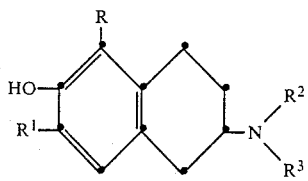

wherein one of R and $R^1$ is H and the other is a carboxamido group, and $R^2$ and $R^3$ are individually H, methyl, ethyl or n-propyl; and pharmaceutically acceptable acid addition salts thereof. These compounds are dopamine agonists and are therefore useful in inhibiting prolactin secretion, alleviating the symptoms of Parkinsonism and reducing blood pressure levels in mammals having elevated blood pressure.

When R is carboxamide and $R^1$ is H, the compounds have the following formula

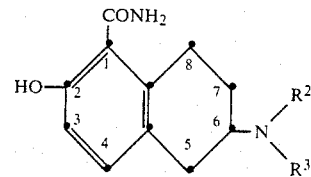

and are named as dl(or ±)-2-hydroxy-6-amino-5,6,7,8-tetrahydronaphthalene-1-carboxamides. When the reverse is true; i.e., R is H and $R^1$ is carboxamide, the ring numbering is also changed and the compounds (Ib)

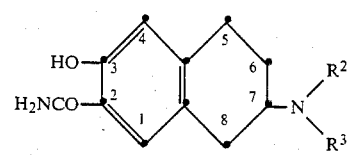

are named as dl(or ±)-3-hydroxy-7-amino-5,6,7,8-tetrahydronaphthalene-2-carboxamides. The "dl" refers to the fact that the carbon carrying the amine function is asymmetric, thereby giving rise to two optical isomers occurring as a racemic mixture. This invention includes within its scope dopamine agonists of formula I, whether as a racemate or as the d or l components thereof.

Also included within the scope of this invention are intermediates useful in preparing the above compounds, said intermediates having the structure

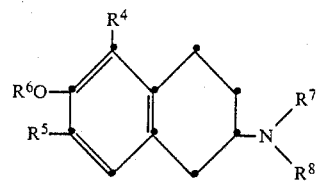

wherein one of $R^4$ and $R^5$ is H and the other is

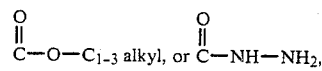

$R^6$ is H or benzyl and $R^7$ and $R^8$ are individually H, methyl, ethyl or n-propyl.

Pharmaceutically-acceptable acid addition salts of the compounds of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylte, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

The compounds of this invention are prepared, by chemically similar routes, the route depending on whether a compound according to Ia or Ib is desired. These routes are set forth in Reaction Schemes A–G below. In the various formulas in the separate reaction schemes, compounds having a single mono-valent substituent [OH, $N_3$, $NH_2$, N(alk)$_2$, etc.] in the tetrahydro portion of the tetrahydronaphthalene; e.g. I, Ia, Ib, VII, VIII, X, XII, XIII, XIV, XV, XXI, XXII, XXIII, XXV, XXVII, XXVIII, XXIX, XXX, XXXVI, XXXIX, XXXX, XXXXI and XXXXII have an asymmetric center at C-6 (in the 1-naphthoates) or at C-7 (in the 2-naphthoates), the point of attachment of the monovalent group. Such compounds exist and are provided herein as a pair of stereoisomers occurring as a racemate.

In certain structures, asymmetric carbons are present at both C-5 and C-6 (in the 1-naphthoic acid series) or at C-7 and C-8 (in the 2-naphthoic acid series); e.g., IX, XIX, XX, XXIV, XXXII, XXXVII and XXXVIII. Compounds with two asymmetric centers exist as four stereoisomers, occurring as two racemic pairs. Formulas bearing the above numbers, while two dimensional, are intended to represent the 3-dimensional individual enantiomers as well as the optically neutral racemates, made up of molecular compounds each containing a pair of stereoisomers.

A convenient preparation of compounds in which the carboxamide group is to be at C-7 (formula I above wherein R is H and $R^1$ is carboxamide, also formula Ib), begins with commercially available 3-hydroxy-2-naphthoic acid. The process of converting this compound to Ib is illustrated in the first part of Reaction Scheme A. As set forth therein, the hydroxy acid is first converted to the corresponding methyl ester (III) according to the procedure of *J.A.C.S.*, 76, 5761 (1954) utilizing dimethyl sulfate in the presence of potassium bicarbonate as the methylating system. Other esterification systems can be used as will be apparent to those skilled in the art, and other lower alkyl esters can be prepared and are equally useful. Hydrogenation of the methyl ester over a palladium-on-carbon catalyst on other suitable noble metal catalyst, such as a platinum or rhodium catalyst, yields a tetralin, methyl 5,6,7,8-tetrahydro-3-hydroxy-2-naphthoate (IV). This 3-hydroxy tetralin-2-ester is then converted to the 3-benzyl ether with benzylchloride in the presence of potassium carbonate, a classical Williamson synthesis. Chromic acid oxidation of the thus-formed methyl 5,6,7,8-tetrahydro-3-benzyloxy-2-naphthoate (V) yields methyl 5,6,7,8-tetrahydro-3-benzyloxy-8-oxo-2-naphthoate (VI).

Reaction Scheme B gives the remainder of this first synthetic route. The reaction of the carbonyl compound (VI) with hydroxylamine hydrochloride produces the corresponding oxime (XVI). The oxime is next acylated with an aryl sulfonylchloride such as benzenesulfonylchloride or p-tosylchloride to yield the aryl sulfonyloxy derivative (XVII). This derivative, upon treatment with a base such as potassium ethylate, rearranges to yield methyl dl-5,6,7,8-tetrahydro-3-benzyloxy-8-oxo-7-amino-2-naphthoate (XXVIII), isolated in the form of its hydrochloride salt. Sodium borohydride reduction of the aminoketone yields the corresponding 8-hydroxy derivative (XIX). At this point, the amino group can be alkylated. For example, to prepare an N,N-di-n-propyl derivative, the amine is reacted with at least 2 moles of propionaldehyde in the presence of sodium cyanoborohydride. To prepare an N,N-dimethyl or N,N-diethyl derivative, formaldehyde and acetaldehyde are used in place of propionaldehyde. The resulting product, methyl dl-5,6,7,8-tetrahydro-3-benzyloxy-8-hydroxy-7-dialkylamino-2-naphthoate (XX) where $R^2$ and $R^3$ are methyl, ethyl or n-propyl, is hydrogenated again using palladium-on-carbon or other suitable noble metal catalyst. This hydrogenation serves to cleave the benzyloxy function to a hydroxyl group and to remove the 8-hydroxy function entirely. The product of this reaction, a methyl dl-N,N-dialkyl-3-hydroxy-7-amino-5,6,7,8-tetrahydro-2-naphthoate (XXI), is then converted to the corresponding amide (Ib) using ammonia in methanol under pressure.

If it is desired to prepare compounds according to Ib where $R^2$ and $R^3$ are H, XIX is reduced and debenzylated as set forth in Reaction Scheme A for conversion of XII to XIII (the hydroxy group is removed in this procedure—see Reaction Scheme B, XX→XXI. The methyl dl-3-hydroxy-7-amino-5,6,7,8-tetrahydro-2-naphthoate thus prepared is readily converted to the naphthalene-2-carboxamide by the procedure of Reaction Scheme B, XXI→Ib, where $R^2$ and $R^3$=H.

Alternatively, as set forth in Reaction Scheme A, methyl 5,6,7,8-tetrahydro-3-benzyloxy-8-oxo-2-naphthoate (VI) can be brominated alpha to the carbonyl group using pyridinium perbromide hydrobromide or other suitable brominating agent including molecular bromine to yield the corresponding 8-oxo-7-bromo derivative (VII). Reaction of this bromo derivative with sodium azide yields methyl dl-5,6,7,8-tetrahydro-3-benzyloxy-8-oxo-7-azido-2-naphthoate (VIII). Reduction with sodium borohydride serves to reduce the oxo group to a hydroxy group (IX) and the hydroxy is removed by treatment with triethylsilane in trifluoroacetic acid (TFA). The resulting 7-azido derivative (X) is then converted to the corresponding 7-amino derivative (XII) by treatment with hydrazine and Raney nickel. At this point, hydrogenation with a palladium catalyst serves to remove the benzyl protecting group and the resulting methyl dl-5,6,7,8-tetrahydro-3-hydroxy-7-amino-2-naphthoate can be converted directly by ammonia in methanol under pressure to yield a compound of this invention, dl-3-hydroxy-7-amino-5,6,7,8-tetrahydronaphthalene-2-carboxamide (Ib where $R^2$ and $R^3$=H). Alternatively, the 7-amino derivative (XII) can be alkylated as with formaldehyde, acetaldehyde or propionaldehyde and sodium cyanoborohydride to yield the 7-N,N-dialkyl derivative (XIV), which derivative after debenzylation with hydrogen over a palladium catalyst followed by conversion of the ester to the amide yields an N,N-dialkyl-3-hydroxy-7-amino-5,6,7,8-tetrahydronaphthalene-2-carboxamide (Ib where $R^2$ and $R^3$ are individually methyl, ethyl or n-propyl.

Reaction Scheme A
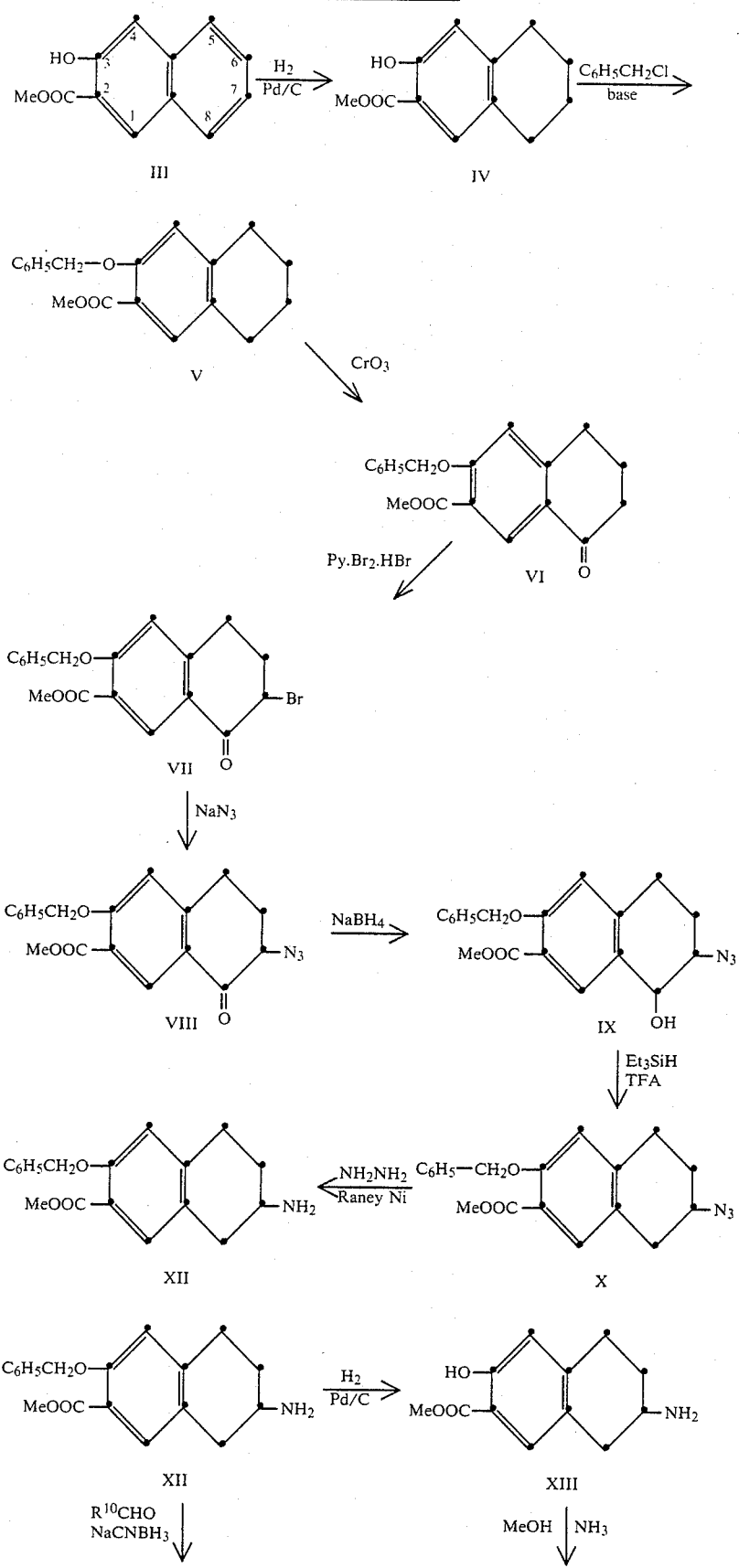

-continued
Reaction Scheme A
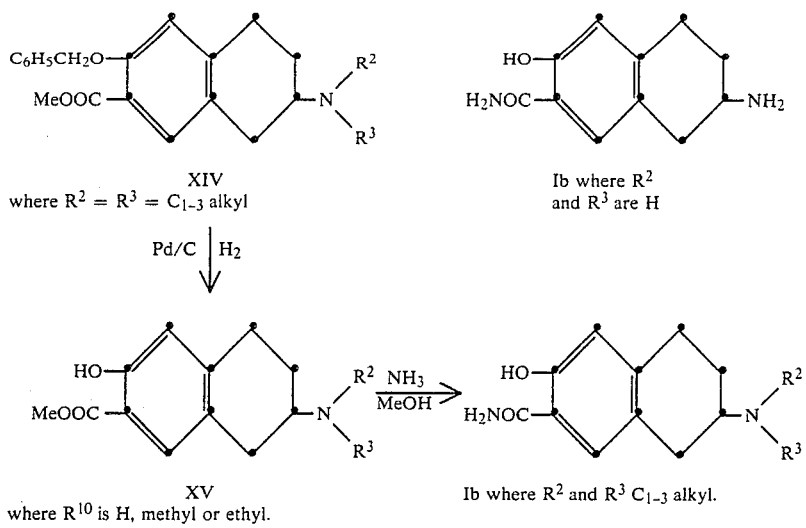
Reaction Scheme B
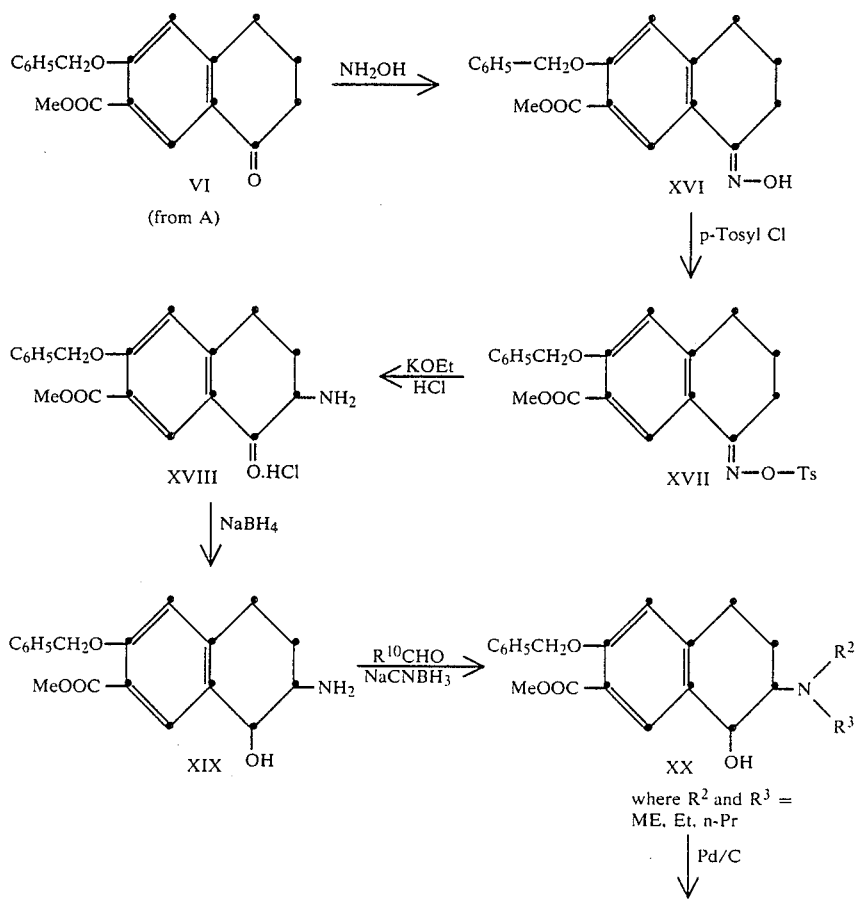

Reaction Scheme B

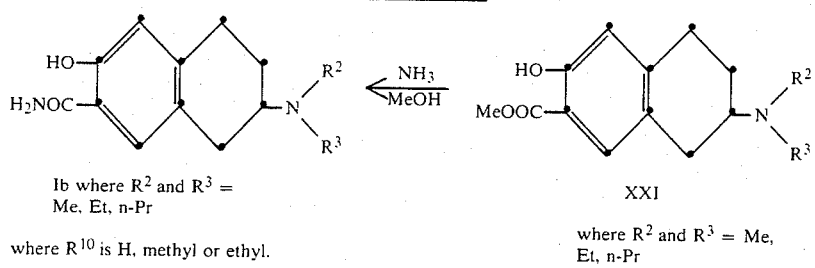

Ib where $R^2$ and $R^3$ = Me, Et, n-Pr where $R^{10}$ is H, methyl or ethyl.

XXI where $R^2$ and $R^3$ = Me, Et, n-Pr

Compounds according to formula I wherein $R^1$ is H and R is carboxamido (Ia) are prepared conveniently according to the procedure of Reaction Scheme C whereby methyl dl-2-benzyloxy-5-oxo-6-bromo-5,6,7,8-tetrahydro-1-naphthoate (XXII)—see *Chem. Pharm. Bull.*, 25, 2999 (1977)—is treated with sodium azide to yield the corresponding 6-azido derivative (XXIII). Reduction of this azide with sodium borohydride yields methyl dl-2-benzyloxy-5-hydroxy-6-azido-5,6,7,8-tetrahydro-1-naphthoate (XXIV). The hydroxyl group is readily removed by treatment with triethylsilane and trifluoroacetic acid to yield methyl dl-2-benzyloxy-6-azido-5,6,7,8-tetrahydro-1-naphthoate (XXV). The 6-azido group is then converted to an amino group by treatment with hydrazine and Raney nickel to provide the corresponding 6-amino derivative (XXVII). The amino derivative can then be alkylated by treatment with a lower alkyl aldehyde (formaldehyde, acetaldehyde, or propionaldehyde) and sodium cyanoborohydride. The resulting compound, a methyl dl-2-benzyloxy-6-dialkylamino-5,6,7,8-tetrahydro-1-naphthoate (XXVIII), upon hydrogenation with palladium-on-carbon, is debenzylated to yield the corresponding 2-hydroxy compound (XXIX). The ester group is then converted with hydrazine to the carboxhydrazide derivative (XXX) which can be split by treatment with Raney nickel to yield a dl-2-hydroxy-6-dialkylamino-5,6,7,8-tetrahydronaphthalene-1-carboxamide (Ia). Alternatively, the 2-hydroxycarboxylic acid ester (XXIX) can be converted directly to the carboxamide (Ia) with methanolic ammonia under pressure.

If it is desired to prepare a compound in which $R^2$ and $R^3$ are both H, the methyl dl-2-benzyloxy-6-amino-5,6,7,8-tetrahydro-1-naphthoate (XXVII) can be directly debenzylated with palladium-on-carbon and hydrogen and the resulting 2-hydroxy derivative converted to the 1-carboxamide either directly with methanolic ammonia or indirectly via the hydrazide (XXIX→XXX→Ia, where $R^2$ and $R^3$=H).

Reaction Scheme C

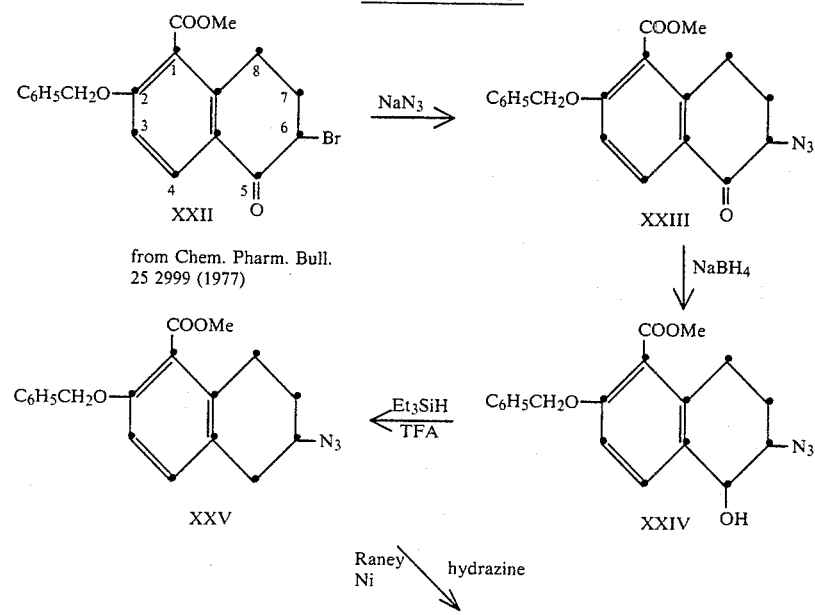

Reaction Scheme C

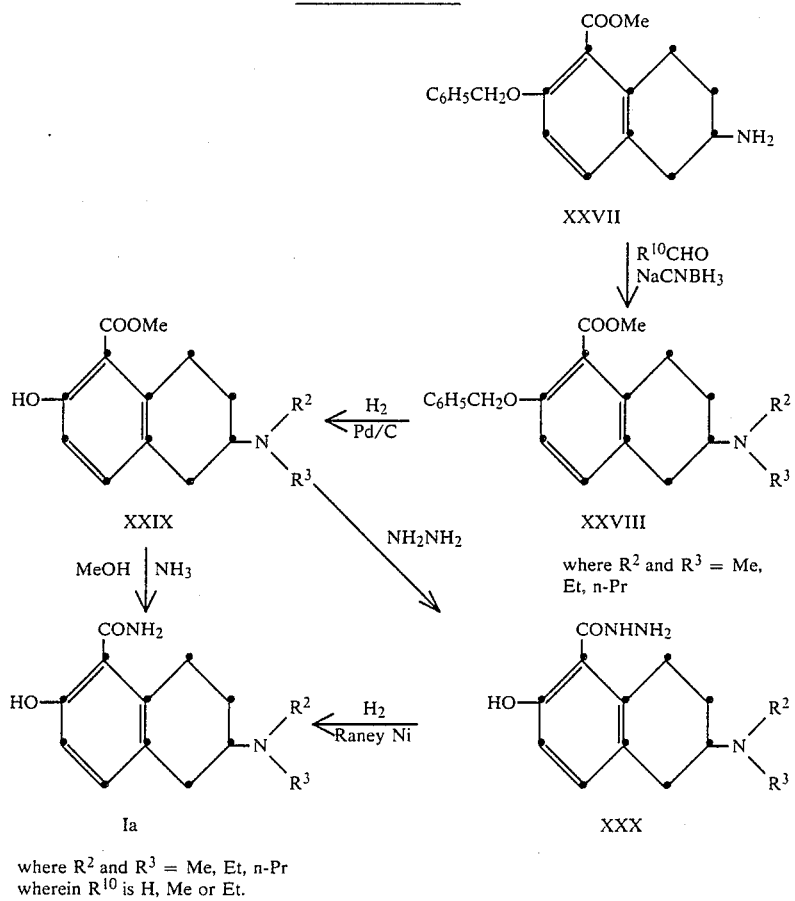

where $R^2$ and $R^3$ = Me, Et, n-Pr
wherein $R^{10}$ is H, Me or Et.

The procedure utilized in *Chem. Pharm. Bull.* (loc. cit.) to yield the bromoketone starting material (XXII) is as follows: 2-hydroxy-1-naphthoic acid, commercially available, is esterified with a lower alkanol. The 2-hydroxy-1-carboxylic acid ester is then hydrogenated over palladium-on-carbon to yield a 2-hydroxytetrahydronaphthoic acid ester. The hydroxy group of this compound is next protected with benzyl group or other suitable protecting group. Chromic acid oxidation yields the corresponding 5-oxo derivative which is then brominated with pyridinium perbromide hydrobromide to yield the aforementioned bromoketone starting material.

Alternatively, the methyl 2-benzyloxy-5-oxo derivative, a precursor to the 6-bromo derivative used as a starting material in the above sequence, can be reduced to the 5-hydroxy compound which can in turn be dehydrated to give a methyl 2-benzyloxy-7,8-dihydro-1-naphthoate (XXXI). The same compound can be prepared from the 5-oxo-6-bromo derivative (XXII) by reduction of the carbonyl group to hydroxyl and removal of the elements of HOBr to yield the 5,6-unsaturated derivative (XXXI). According to Reaction Scheme D, peroxidation of this compound with m-chloroperbenzoic acid or other suitable agent in the presence of ethanol yields a 5-ethoxy-6-hydroxy derivative (XXXII) which compound, on treatment with acid, produces methyl dl-2-benzyloxy-6-oxo-5,6,7,8-tetrahydro-1-naphthoate (XXXXII). The 6-oxoderivative is then converted to the 6-amino derivative (XXVII) with ammonium acetate and sodium cyanoborohydride. Conversion of XXVII to Ia where $R^2$ and $R^3$=alkyl is set forth in Reaction Scheme C.

Reaction Scheme D

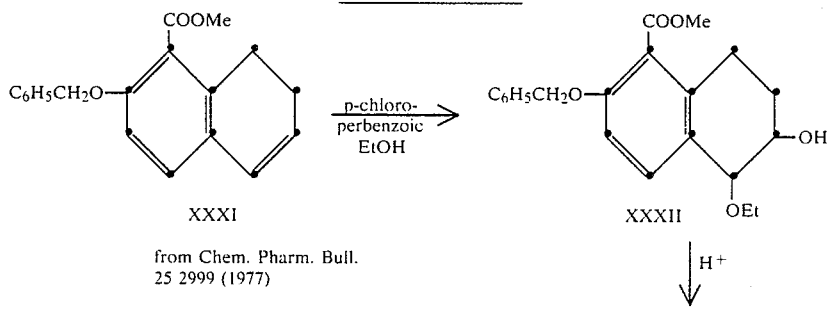

from Chem. Pharm. Bull.
25 2999 (1977)

Reaction Scheme D

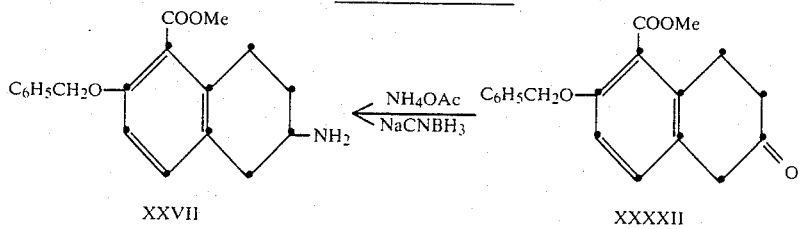

In a still different procedure (Reaction Scheme E below), in which the order of steps is somewhat changed, the methyl dl-2-benzyloxy-6-azido-5,6,7,8-tetrahydro-1-naphthoate (XXV) can be treated with ammonia in methanol under pressure to yield the corresponding dl-2-benzyloxy-6-azido-5,6,7,8-tetrahydronaphthalene-1-carboxamide (XXXIX). Conversion compound of this invention (Ib) where $R^2$ and $R^3$ are individually Me, Et or n-Pr.

It is apparent that Reaction Schemes A and B can be similarly modified by preparing the carboxamide function early in the procedure rather than as a last step, and other necessary reactions carried out on the carboxamide.

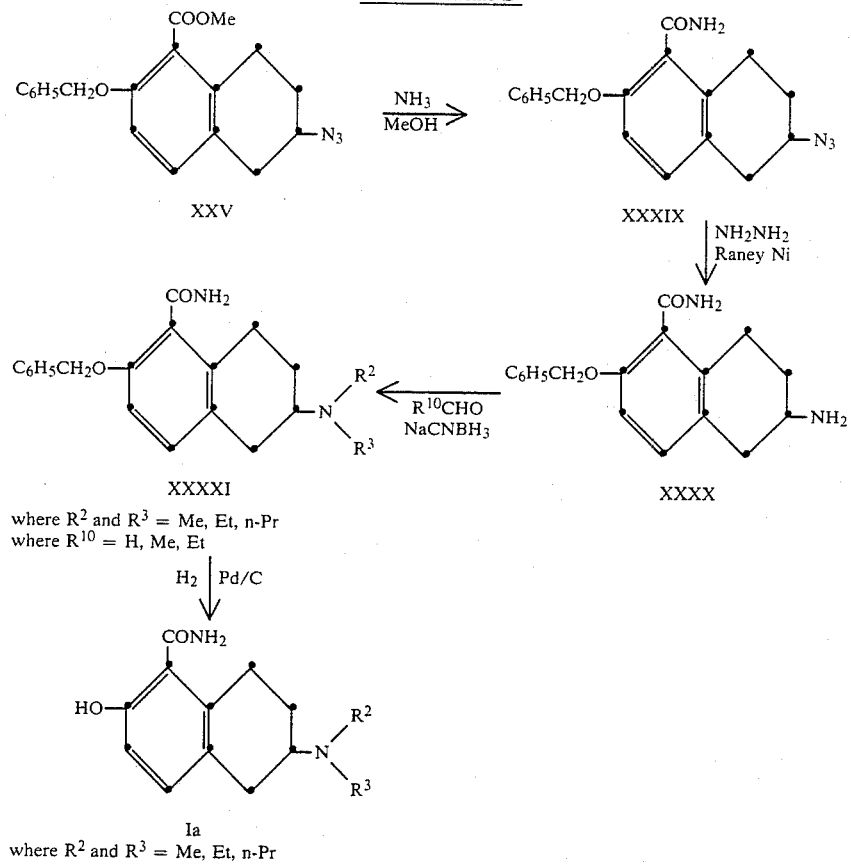

Reaction Scheme E of the azide group to an amino group with hydrazine and Raney nickel yields a dl-2-benzyloxy-6-amino-5,6,7,8-tetrahydronaphthalene-1-carboxamide (XXXXI). This compound can be treated directly with hydrogen in the presence of a palladium catalyst to remove the benzyl group and yield a compound according to formula Ib above wherein $R^2$ and $R^3$ are both hydrogen. Alternatively, the benzyloxy derivative can be alkylated with a lower aldehyde and sodium cyanoborohydride to yield a dl-2-benzyloxy-6-dialkylamino-5,6,7,8-tetrahydronaphthalene-1-carboxamide (XXXXI) which compound, upon treatment with hydrogen in the presence of a palladium catalyst, yields a Alternatively, following one of the procedures utilized to prepare compounds according to Ib above as set forth in Reaction Scheme F below, the 2-benzyloxy-5-oxo-5,6,7,8-tetrahydro-1-naphthoate ester (XXXIII) (Scheme F) can be converted to the corresponding oxime (XXXIV) with hydroxylamine hydrochloride and the oxime acylated with an aryl sulfonylchloride (XXXV). Rearrangement of the acyloxime with base yields the 5-oxo-6-amino derivative (XXXVI). This compound is then reduced to the corresponding 5-hydroxy compound (XXXVII). The amine group can then be optionally alkylated with an aldehyde and sodium cyanoborohydride (XXXVIII). Finally, the benzyl group and the 5-hydroxy group are both removed with hydrogen in the presence of a palladium catalyst to yield, after ammonolysis of the ester function, a compound of this invention (Ia) where $R^2$ and $R^3$ are alkyl.

with a protected ortho-benzyloxy group (here, the 1-naphthoate derivative XXV) to the dl-2-hydroxy-6-amino-1-naphthalenecarboxamide, via the free acid, acid chloride and amide followed by reduction of the azide group to $NH_2$ and lastly by debenzylation to the free 2-OH derivative.

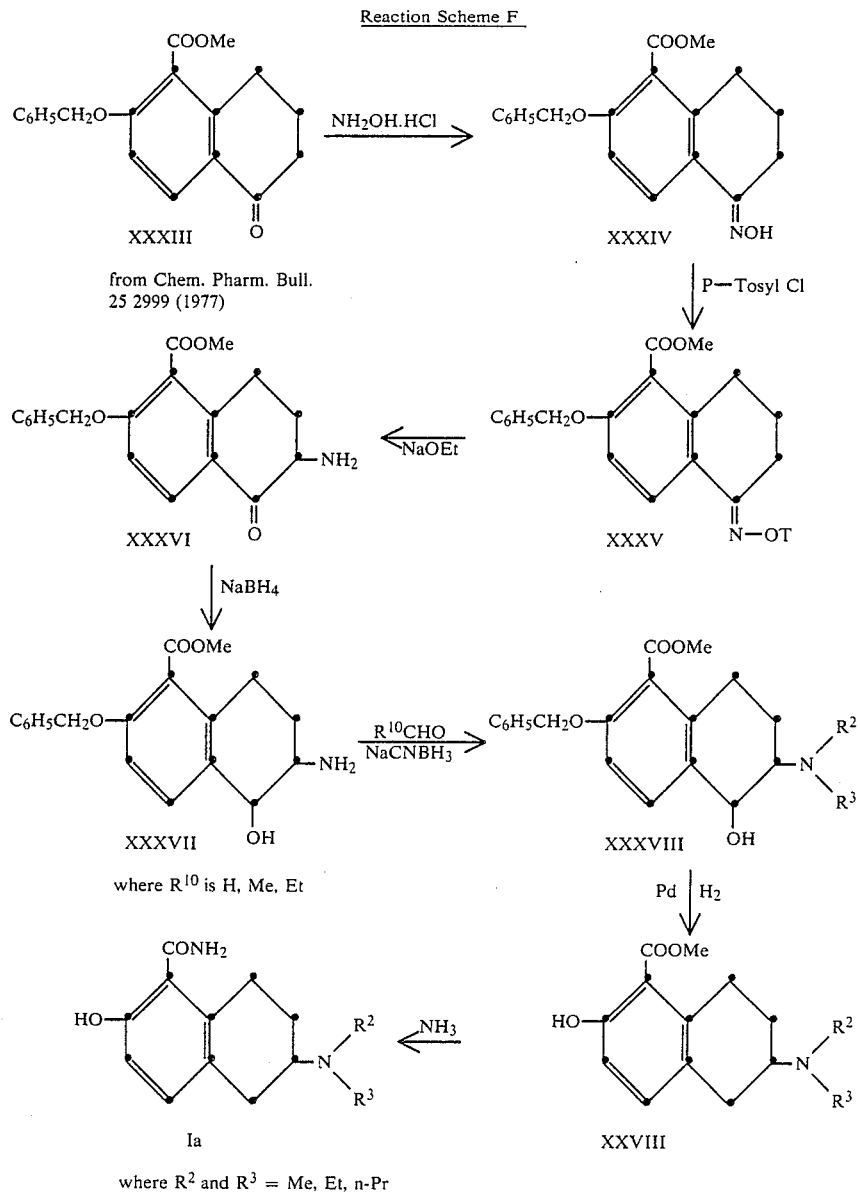

Finally, Reaction Scheme G illustrates an alternative procedure for proceding from an azido naphthoate ester

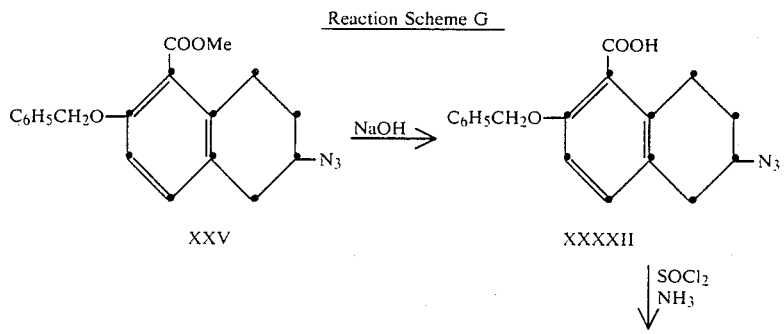

Reaction Scheme G

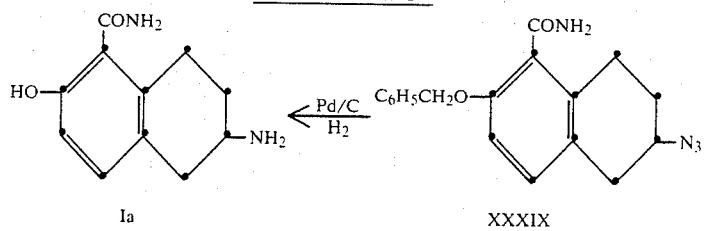

where $R^2$ and $R^3$ = H.

In the above Reaction Sequences A-G, alkylation of the 6(7)-amino group has been illustrated only to produce symmetrical dialkyl derivatives ($R^2=R^3=$Me, Et, n-Pr). If it is desired to produce monoalkyl derivatives or unsymmetrical dialkyl derivatives ($R^2 \neq R^3$), such derivatives being included within the scope of formulas I, Ia and Ib, the following general procedure is employed. First, the 6(7)-amino group is mono alkylated by using equimolar quantities of aldehyde and amine plus an excess of sodium cyanoborohydride. The secondary amine thus produced, after debenzylation and amidation, has a structure according to I wherein one of R and $R^1$ is H and the other is carboxamide, and one of $R^2$ and $R^3$ is H and the other is Me, Et or n-Pr. The aldehyde-cyanoborohydride procedure can thus be repeated, if desired, on the secondary amino compound with a different aldehyde so as to produce a compound according to I wherein $R^2$ and $R^3$ are not the same but are individually Me, Et or n-Pr.

This invention is further exemplified by the following specific examples.

EXAMPLE 1

Preparation of dl-2-hydroxy-6-dimethylamino-5,6,7,8-tetrahydro-1-naphthalenecarboxamide A solution was prepared by dissolving 8.9 g. of methyl 2-benzyloxy-5-oxo-5,6,7,8-tetrahydro-1-napthoate prepared by the procedure of Chem. Pharm. Bull., 25, 2999 (1977) in 150 ml. of methanol and 150 ml. of tetrahydrofuran (THF). Nine and six tenths grams of pyridinium perbromide hydrobromide were added and the reaction mixture stirred for about three hours, after which time it was diluted with water and the resulting aqueous mixture extracted with chloroform. The chloroform layer was separated and the separated layer washed with saturated sodium chloride and then dried. Evaporation yielded methyl dl-2-benzyloxy-5-oxo-6-bromo-5,6,7,8-tetrahydro-1-naphthoate as a residue. The residue was dissolved in 200 ml. of dimethyl formamide (DMF) containing 5 ml. of glacial acetic acid. This solution was cooled to about 0° C. A solution containing 4 g. of sodium azide in 40 ml. of water was then added. The resulting reaction mixture was stirred and cooled for about four hours and then left at about 0°–5° C. overnight. It was then diluted with water and the aqueous mixture extracted with ethyl acetate. The ethyl acetate layer was separated and the separated layer washed with saturated aqueous sodium chloride and then dried. Evaporation of the residue yielded methyl dl-2-benzyloxy-5-oxo-6-azido-5,6,7,8-tetrahydro-1-naphthoate formed in the above reaction.

The compound melted at 65°–7° C. with decomposition after crystallization from methanol.

Analysis Calculated: C, 64.95; H, 4.88; N, 11.96. Found: C, 64.64; H, 4.98; N, 12.02.

The 6-azido compound was dissolved in about 200 ml. of methanol and the methanol solution cooled to about 0° C. Nine grams of sodium borohydride were added thereto in small portions with stirring. The reaction mixture was next stirred for about four hours and then diluted with water. The aqueous mixture was extracted several times with equal volumes of chloroform. The chloroform extracts were combined and the combined extracts washed with saturated sodium chloride and then dried. Evaporation of the chloroform yielded methyl dl-2-benzyloxy-5-hydroxy-6-azido-5,6,7,8-tetrahydronaphthoate formed in the above reaction. TLC over silica (ether) indicated that the solid residue was substantially the desired product containing a small amount of starting material. Eleven grams of a viscous oil which crystallized after standing overnight were obtained. Methyl dl-2-benzyloxy-5-hydroxy-6-azido-5,6,7,8-tetrahydro-1-naphthoate thus prepared melted at 65°–66° C. after recrystallization from ether.

Analysis Calculated: C, 64.58; H, 5.42; N, 11.89. Found: C, 64.60; H, 5.33; N, 11.85.

Five Hundred milligrams of methyl dl-2-benzyloxy-5-hydroxy-6-azido-5,6,7,8-tetrahydro-1-naphthoate were suspended in 10 ml. of triethylsilane and 10 ml. of carbon tetrachloride. About 5 ml. of trifluoroacetic acid were added. TLC after a ten minute reaction time indicated that there was no longer any starting material present and that there was only one major component in the reaction mixture. After 25 minutes reaction time, the reaction mixture was poured over ice and the aqueous solution made basic with 14N aqueous ammonium hydroxide. The alkaline layer was extracted with chloroform. The chloroform extract was separated, washed with saturated sodium chloride and dried and the solvent removed by evaporation. The residue was chromatographed over 30 g. of florisil using hexane containing increasing amounts (0–20%) of ether as the eluant. Fractions shown by TLC to contain the desired product, methyl dl-2-benzyloxy-6-azido-5,6,7,8-tetrahydro-1-naphthoate, were combined. Evaporation of the solvent from the combined fractions yielded purified methyl dl-2-benzyloxy-6-azido-5,6,7,8-tetrahydro-1-naphthoate which melted at 83°–4° C. after recrystallizaton from hexane; yield=365 mg.

Analysis Calculated: C, 67.64; H, 5.68; N, 12.46. Found: C, 67.93; H, 5.71; N, 12.56.

The above reaction in which the 5-hydroxy group was eliminated by using a triethylsilane-trifluoroacetic acid reagent was repeated on a 4.4 g. sample of methyl dl-2-benzyloxy-5-hydroxy-6-azido-5,6,7,8-tetrahydronaphthoate. The 6-azido compound from this reaction was used without further purification as follows:

the residue from evaporation of the extracting solvent was dissolved in 100 ml. of THF and 100 ml. of ethanol. About 3 g. of Raney nickel were added. Next, a solution of 2 ml. of hydrazine hydrate in 10 ml. of ethanol was added in dropwise fashion to the stirred reaction mixture. The reaction mixture was filtered and the volatile constituents removed by evaporation. This residue was dissolved in 200 ml. of methanol. One gram of sodium cyanoborohydride was added followed by 10 ml. of 37% aqueous formaldehyde. The reaction mixture was stirred at room temperature under a nitrogen atmosphere overnight and was then diluted with saturated aqueous sodium bicarbonate. The alkaline aqueous mixture was extracted with chloroform. The chloroform extract was separated and the separated extract washed with saturated aqueous sodium chloride and then dried. Evaporation of the solvent yielded a residue which, by TLC, indicated one major product contaminated with a small amount of starting material. A chloroform solution of the residue was chromatographed over 100 g. of florisil using chloroform containing increasing amounts (0–4%) of methanol as the eluant. Fractions shown by TLC to contain the desired product, methyl dl-2-benzyloxy-6-dimethylamino-5,6,7,8-tetrahydro-1-naphthoate, were combined in ethanol solution and the solution saturated with gaseous hydrogen chloride. The crystalline hydrochloride salt was separated by filtration and recrystallized from an ethanol/ether solvent mixture. One and seven tenths grams of hydrochloride salt melting at 190°–2° C. were obtained.

Analysis Calculated: C, 67.10; H, 6.97; N, 3.73; Cl, 9.43. Found: C, 66.85; H, 7.12; N, 3.74; Cl, 9.36.

Two and thirty-eight hundredths grams of methyl dl-2-benzyloxy-6-dimethylamino-5,6,7,8-tetrahydro-1-naphthoate hydrochloride were dissolved in 50 ml. of methanol and hydrogenated with 1 g. of palladium-on-carbon in 10 ml. of THF at a hydrogen pressure=60 psi. After the theoretical quantity of hydrogen had been absorbed, the reaction mixture was taken from the hydrogenator and filtered. Evaporation of the solvent in vacuo yielded, as a residue, methyl dl-2-hydroxy-6-dimethylamino-5,6,7,8-tetrahydro-1-naphthoate hydrochloride formed in the above reaction. One and five tenths grams of a solid were obtained which decomposed at about 225° C.

Analysis Calculated: C, 58.84; H, 7.05; N, 4.90; Cl, 12.41. Found: C, 59.08; H, 7.34; N, 5.00; Cl, 12.26.

The solid hydrochloride salt obtained above was dissolved in water and dilute aqueous sodium bicarbonate added until the aqueous layer became basic. The aqueous layer was extracted several times with an equal volume of a chloroform/isopropanol solvent mixture. The organic extracts were combined and the combined extracts washed with saturated aqueous sodium chloride and then dried. Evaporation of the solvent in vacuo yielded 1.20 g. of an oil comprising methyl dl-2-hydroxy-6-dimethylamino-5,6,7,8-tetrahydro-1-naphthoate free base. The oil was dissolved in a 60 ml. of methanol to which was added 10 ml. of anhydrous hydrazine. The reaction mixture was heated to refluxing temperature for about one day and then cooled. The volatile constituents were removed in vacuo and the residue, comprising dl-2-hydroxy-6-dimethylamino-5,6,7,8-tetrahydro-1-naphthalenecarboxhydrazide formed in the above reaction, was dissolved in 125 ml. of ethanol to which were added about 2 g. of Raney nickel. This reaction mixture was heated to refluxing temperature for about one day after which time it was cooled and filtered. Gaseous HCl was passed into the solution. The volatile constituents were evaporated in vacuo and the residue recrystallized from ethanol. Four hundred and seventy mg. of dl-2-hydroxy-6-dimethylamino-5,6,7,8-tetrahydro-1-naphthalenecarboxamide hydrochloride were obtained melting at 249°–251° C. with decomposition.

Analysis Calculated: C, 57.67; H, 7.07; N, 10.35; Cl, 13.09. Found: C, 58.00; H, 7.27; N, 10.62; Cl, 12.92.

EXAMPLE 2

Preparation of dl-2-Hydroxy-6-di-n-propylamino-5,6,7,8-tetrahydro-1-naphthalenecarboxamide Following the procedure of Example 1, 4.0 g. of methyl dl-2-benzyloxy-5-hydroxy-6-azido-5,6,7,8-tetrahydro-1-naphthoate were treated with a mixture of triethylsilane and trifluoroacetic acid in carbon tetrachloride solution to yield methyl dl-2-benzyloxy-6-azido-5,6,7,8-tetrahydro-1-naphthoate. Still following the procedure of Example 1, this compound was reacted with hydrazine hydrate and Raney nickel in THF and ethanol to yield methyl dl-2-benzyloxy-6-amino-5,6,7,8-tetrahydro-1-naphthoate. The 6-amino compound was dissolved in 200 ml. of methanol to which was added 1 g. of sodium cyanoborohydride followed by 10 ml. of propionaldehyde. The reaction mixture was stirred at room temperature under a nitrogen blanket overnight, and was then diluted with saturated aqueous sodium bicarbonate solution. The alkaline layer was extracted with chloroform. The chloroform extract was separated and the separated extract washed with saturated aqueous sodium chloride and then dried. Evaporation of the solvent in vacuo yielded a residue which was dissolved in chloroform and the chloroform solution chromatographed over 100 g. of florisil using chloroform containing increasing quantities (0–2%) of methanol as the eluant. Fractions containing methyl dl-2-benzyloxy-6-di-n-propylamino-5,6,7,8-tetrahydro-1-naphthoate were combined and the solvent evaporated from the combined fractions. The resulting residue was converted to the hydrochloride salt which melted at 170°–1° C. after recrystallization from an ethanol/ether solvent mixture; yield=3.41 g.

Analysis Calculated: C, 69.51; H, 7.93; N, 3.24; Cl, 8.21. Found: C, 69.27; H, 7.66; N, 3.42; Cl, 7.94.

The product was debenzylated by hydrogenation in the presence of a palladium catalyst and the debenzylated compound converted to the amide by the procedure of Example 1.

EXAMPLE 3

Preparation of dl-3-Hydroxy-7-di-n-propylamino-5,6,7,8-tetrahydro-2-naphthalenecarboxamide A reaction mixture was prepared from 200 g. of 3-hydroxy-2-naphthoic acid, 160 g. of potassium bicarbonate, 154 g. of dimethyl sulfate and 1500 ml. of acetone. The reaction mixture was heated to refluxing temperature for about 3 hours after which time it was diluted with water and the resulting alkaline aqueous layer extracted with ethyl acetate. The ethyl acetate layer was separated and the separated layer washed with water and saturated aqueous sodium chloride and then dried. Evaporation of the solvent yielded a residue which solidified upon trituration with methanol to yield 205 g. of methyl 3-hydroxy-2-naphthoate melting at 72°–4° C.

Two hundred and twenty-two grams of the above ester were hydrogenated at 1500 psi using 80 g. of a 5% palladium-on-carbon catalyst and 1.45 l. of methanol as a solvent. The hydrogenation was carried out at 70° C. and took six hours. The hydrogenation mixture was cooled and the catalyst removed by filtration. The solvent was removed from the filtrate by evaporation to yield two crystalline fractions (total yield = 144.5 g.) of methyl 3-hydroxy-5,6,7,8-tetrahydro-2-naphthoate melting at 41°–2° C.

Analysis Calculated: C, 69.81; H, 6.84. Found: C, 70.13; H, 6.93.

A reaction mixture was prepared from the above quantity of ester, 50 g. of potassium carbonate, 46 g. of benzylchloride and 400 ml. of dimethylactamide (DMA). After the reaction had gone to completion, the reaction mixture was filtered through florisil and the precipitate of methyl 3-benzyloxy-5,6,7,8-tetrahydro-2-naphthoate which formed was crystallized from ethanol to yield 142.7 g. of compound melting at 60°–3° C.

Analysis Calculated: C, 77.00; H, 6.80. Found: C, 77.26; H, 6.99.

A solution of 142 g. of the above ether-ester in 600 ml. of glacial acetic acid was chilled. A second solution of 100 g. of $CrO_3$ in 280 ml. of glacial acetic acid and 40 ml. of $H_2O$ was added to the first in dropwise fashion. The reaction was stirred and cooled (0°–5° C.) for about 3 hrs., after which time excess $CrO_3$ was destroyed by the addition of isopropanol. The reaction mixture was diluted with $H_2O$ and the aqueous mixture extracted with ethyl acetate. The ethyl acetate extract was separated and washed successively with water, saturated aqueous sodium bicarbonate, water, and saturated aqueous sodium chloride. The ethyl acetate solution was dried. Concentration of the solution yielded solid methyl 3-benzyloxy-8-oxo 5,6,7,8-tetrahydro-2-naphthoate melting at 111°–4° C.; yield = 58 g. An additional 35 g. were obtained from the filtrate, utilizing chromatography to remove impurities.

Forty-Three grams of methyl 3-benzyloxy-8-oxo-5,6,7,8-tetrahydro-2-naphthoate were suspended in 1 l. of methanol to which was added 14 g. of hydroxylamine hydrochloride. Sixteen grams of sodium acetate were then added. The reaction mixture was stirred at ambient temperature under a nitrogen blanket for about one day after which time it was diluted with water and the aqueous layer extracted with ethyl acetate. The ethyl acetate layer was separated, the separated layer washed with water and saturated aqueous sodium chloride and then dried. Evaporation of the solvent yielded 49 g. of methyl 3-benzyloxy-8-oximino-5,6,7,8-tetrahydro-2-naphthoate melting at 148°–150° C. after recrystallization from ether.

Analysis Calculated: C, 70.14; H, 5.89; N, 4.31. Found: C, 70.33; H, 5.88; N, 4.49.

Forty-Nine grams of methyl 3-benzyloxy-8-oximino-5,6,7,8-tetrahydro-2-naphthoate were dissolved in 300 ml. of pyridine and the solution cooled to about 0° C. Twenty-three ml. of benzenesulfonylchloride were added slowly. After the addition had been completed, the reaction mixture was stirred at about 0° C. for about 1.75 hours. The reaction mixture was kept at 0°–5° C. overnight and was then diluted with water and the resulting aqueous mixture extracted with chloroform. The organic layer was separated and the separated layer washed with saturated aqueous sodium chloride and then dried. Evaporation of the solvent in vacuo yielded a residue which was dissolved in chloroform and the chloroform solution filtered through 300 g. of florisil. TLC showed one major spot. The residue from the florisil filtration procedure was recrystallized from ether to yield 51 g. of methyl 3-benzyloxy-8-O-benzenesulfoximino-5,6,7,8-tetrahydro-2-naphthoate formed in the above reaction melting at 125°–8° C. Recrystallization from methanol yielded crystals melting 171°–2° C. An additional 2 g. of material were obtained from the mother liquors.

Analysis Calculated: C, 64.50; H, 4.98; N, 3.01; S, 6.89. Found: C, 64.74; H, 5.06; N, 2.95; S, 6.78.

The benzenesulfoximino compound was rear-ranged with alkali according to the following procedure: One and five tenths grams of methyl 3-benzyloxy-8-benzenesulfonyloximino-5,6,7,8-tetrahydro-2-naphthoate were dissolved in 40 ml. of toluene. This solution was added dropwise to a solution of potassium ethylate prepared by adding 0.2 g. of potassium to 25 ml. of ethanol. The reaction mixture was maintained in the range 0°–5° C. at which temperature it was stirred for about 1.5 hours after the addition had been completed. The reaction mixture was kept in the refrigerator for 48 hours after which time it was diluted with ethyl acetate and the separated ethyl acetate layer washed with water. The ethyl acetate layer was dried and the ethyl acetate removed by evaporation in vacuo. TLC showed one major spot. The residue was dissolved in methanol, and the hydrochloride salt was prepared by passing gaseous hydrogen chloride into a methanolic solution of the base. Recrystallization of the hydrochloride salt from a methanol/ether solvent mixture yielded 290 mg. of methyl dl-3-benzyloxy-7-amino-8-oxo-5,6,7,8-tetrahydro-2-naphthoate hydrochloride melting at 195°–200° C.

Analysis Calculated: C, 63.07; H, 5.57; N, 3.87; Cl, 9.80. Found: C, 62.95; H, 5.49; N, 4.10; Cl, 10.06.

A suspension of 2 g. of sodium borohydride was prepared in 100 ml. of ethanol. Two and two tenths grams of methyl dl-3-benzyloxy-7-amino-8-oxo-5,6,7,8-tetrahydro-2-naphthoate hydrochloride were added thereto in portions. The reaction mixture was stirred for two hours and was then diluted with water and the aqueous mixture extracted several times with equal volumes of chloroform. The chloroform extracts were combined and the combined extracts washed with saturated aqueous sodium chloride and then dried. Evaporation of the chloroform yielded a residue comprising methyl dl-3-benzyloxy-7-amino-8-hydroxy-5,6,7,8-tetrahydro-2-naphthoate hydrochloride formed in the above reaction. One and forty-one hundredths grams of the hydrochloride salt melting at 160°–5° C. were obtained. Recrystallization from ethanol yielded crystals melting at 172°–5° C.

Analysis Calculated: C, 62.72; H, 6.09; N, 3.85; Cl, 9.74. Found: C, 62.90; H, 6.33; N, 3.77; Cl, 9.54.

Two and eighteen hundredths grams of methyl dl-3-benzyloxy-7-amino-8-hydroxy-5,6,7,8-tetrahydro-2-naphthoate hydrochloride, 500 mg. of sodium acetate, 380 mg. of sodium cyanoborohydride, 4 ml. of propionaldehyde and 150 ml. of methanol were placed in a reaction vessel which was stirred under a nitrogen atmosphere for about 19 hours. The reaction mixture was then diluted with 1N aqueous hydrochloric acid. The aqueous acidic layer was washed with ether, the ether wash being discarded, and was then made basic with 14N ammonium hydroxide. The resulting alkaline aqueous layer was extracted several times with equal volumes of chloroform. The chloroform extracts were combined and the combined extracts washed with saturated aqueous sodium chloride and then dried. Evaporation of the chloroform yielded a residue which, by TLC, showed one major spot. The residue was dissolved in chloroform and the chloroform solution chromatographed over 35 g. of florisil using chloroform containing small quantities of methanol as the eluant. Fractions shown by TLC to contain methyl dl-3-benzyloxy-7-di-n-propylamino-8-hydroxy-5,6,7,8-tetrahydro-2-naphthoate were combined and the solvent evaporated therefrom. The resulting residue was dissolved in ethanol and gaseous hydrogen chloride passed into the ethanolic solution thus forming the hydrochloride salt. Recrystallization of the solid hydrochloride salt yielded 1.55 g. of methyl dl-3-benzyloxy-7-di-n-propylamino-8-hydroxy-2-naphthoate hydrochloride melting at 199°–200° C.

Analysis Calculated: C, 67.03; H, 7.65; N, 3.13; Cl, 7.91. Found: C, 66.98; H, 7.76; N, 3.02; Cl, 7.61.

One and five tenths grams of methyl dl-3-benzyloxy-7-di-n-propylamino-8-hydroxy-5,6,7,8-tetrahydro-2-naphthoate hydrochloride were dissolved in 5 ml. of water and 50 ml. of methanol. One gram of palladium-on-carbon was added and the resulting mixture was hydrogenated at 60 psi at a temperature of about 50° C. After the hydrogenation was complete, the hydrogenation mixture was filtered to remove the catalyst and the solvent evaporated from the filtrate. The thus-obtained residue was suspended in dilute aqueous sodium bicarbonate and the bicarbonate suspension extracted several times with equal volumes of chloroform. The chloroform extracts were combined and the combined extracts washed with saturated aqueous sodium chloride and then dried. Evaporation of the solvent yielded methyl dl-3-hydroxy-7-di-n-propylamino-5,6,7,8-tetrahydro-2-naphthoate. The hydrochloride salt was prepared in ethanol solution, during which time a trans-esterification reaction apparently occurred since the product isolated was ethyl dl-3-hydroxy-7-di-n-propylamino-5,6,7,8-tetrahydro-2-naphthoate hydrochloride. Four hundred and ten mg. of the hydrochloride salt melting at 202°–4° C. were obtained after recrystallization from an ethanol/ether solvent mixture.

Mass spectrum: molecular ion at 319.

Analysis Calculated: C, 64.12; H, 8.50; N, 3.94; Cl, 9.96. Found: C, 63.47; H, 8.10; N, 4.35; Cl, 10.15.

Three hundred sixty mg. of ethyl dl-3-hydroxy-7-di-n-propylamino-5,6,7,8-tetrahydro-2-naphthoate hydrochloride were dissolved in 100 ml. of methanol and the methanolic solution cooled to about 0° C. The cooled solution was then saturated with gaseous ammonia. The amidation mixture was left at ambient temperature under essentially anhydrous conditions for about 5 days. The course of the reaction was followed during this time by TLC which showed increasing amounts of a more polar material, presumably the carboxamide, and lesser amounts of starting material. Evaporation of the reaction mixture in vacuo yielded a solid material which melted at 272°–4° C. with decomposition after recrystallization from ethanol; yield=280 mg. of dl-3-hydroxy-7-di-n-propylamino-5,6,7,8-tetrahydro-2-naphthalenecarboxamide.

Analysis Calculated: C, 62.47; H, 8.33; N, 8.57; Cl, 10.85. Found: C, 62.26; H, 8.26; N, 8.50; Cl, 10.69.

The alkylation of 3-benzyloxy-7-amino-8-hydroxy-5,6,7,8-tetrahydro-2-naphthoate methyl ester hydrochloride was repeated replacing propionaldehyde with formaldehyde. Methyl dl-3-benzyloxy-7-dimethylamino-8-hydroxy-5,6,7,8-tetrahydro-2-naphthoate hydrochloride thus prepared melted at 192°–3° C. after recrystallization from ethanol.

Analysis Calculated: C, 64.36; H, 6.69; N, 3.57; Cl, 9.05. Found: C, 64.61; H, 6.76; N, 3.68; Cl, 8.81.

The compound was converted to dl-3-hydroxy-7-dimethylamino-5,6,7,8-tetrahydro-2-naphthalenecarboxamide by the above procedures.

Following the above procedure, but starting with 59 g. of methyl 2-benzyloxy-5-oxo-5,6,7,8-tetrahydro-1-naphthoate, 43 g. of methyl 2-benzyloxy-5-oximino-5,6,7,8-tetrahydro-1-naphthoate were obtained melting at 178°–180° C.

Methyl 2-benzyloxy-5-benzenesulfonyloximino-5,6,7,8-tetrahydro-1-naphthoate was next prepared and melted at 135°–7° C.; yield=46.5 g. from 40 g. of oximino compound.

Fifty grams of methyl 2-benzyloxy-5-benzenesulfonyloximino-5,6,7,8-tetrahydro-1-naphthoate were treated with potassium ethylate in toluene solution to yield about 22 g. of methyl dl-2-benzyloxy-5-oxo-6-amino-5,6,7,8-tetrahydro-1-naphthoate hydrochloride melting at about 220° C. with decomposition after recrystallization from ethanol.

Twenty-two and four tenths grams of methyl dl-2-benzyloxy-5-oxo-6-amino-5,6,7,8-tetrahydro-1-naphthoate hydrochloride were reduced with sodium borohydride in ethanol to produce the corresponding 5-hydroxy compound isolated as a hydrochloride salt. This compound was alkylated with propionaldehyde in the presence of sodium cyanoborohydride in methanol solution to yield methyl dl-2-benzyloxy-5-hydroxy-6-di-n-propylamino-5,6,7,8-tetrahydro-1-naphthoate as the hydrochloride salt. (8.3 g.) melting at about 215°–6° C.

Analysis Calculated: C, 67.03; H, 7.65; N, 3.13; Cl, 7.91. Found: C, 66.75; H, 7.44; N, 3.25; Cl, 7.71.

Hydrogenation of this compound with palladium-on-carbon in methanol at about 60 psi and 50° C. gave methyl dl-2-hydroxy-6-di-n-propylamino-5,6,7,8-tetrahydro-1-naphthoate hydrochloride (2.1 g. of starting material yielded 710 mg. of hydrochloride salt) M.P.=195°–6° C. after recrystallization from an ether/ethanol solvent mixture.

Analysis Calculated: C, 63.24; H, 8.26; N, 4.10; Cl, 10.37. Found: C, 63.04; H, 8.27; N, 4.33; Cl, 10.56.

This ester is readily converted to the corresponding carboxamide by the procedure of Example 1.

EXAMPLE 4

Alternate preparation of dl-2-Hydroxy-6-amino-5,6,7,8-tetrahydronaphthalene-1-carboxamide One-half gram of methyl dl-2-benzyloxy-6-azido-5,6,7,8-tetrahydro-1-naphthoate (from Example 1) were dissolved in 20 ml. of ethanol to which were added 20 ml. of 50% (w/v) aqueous sodium hydroxide. This mixture was heated at about 100° C. for 18 hours, after which time the reaction mixture was poured into an ice-water mixture. Sufficient 12N aqueous hydrochloric acid was added to make the reaction mixture acidic. dl-2-Benzyloxy-6-azido-5,6,7,8-tetrahydro-1-naphthoic acid formed in the above reaction, being insoluble in the acidic layer, separated and was dissolved with several 3:1 chloroform/isopropanol extracts. The organic extracts were combined and the combined extracts washed with saturated aqueous sodium chloride and then dried. Evaporation of the solvent in vacuo yielded a dark viscous oil which was dissolved in chloroform and the chloroform solution chromatographed over silica gel using chloroform containing increasing quantities (0–5%) of methanol as the eluant. Fractions shown by TLC to contain the desired naphthoic acid were combined and the solvent removed therefrom. The residual golden yellow oil thus obtained was dissolved in ether and hexane added to the ethereal solution to the point of incipient precipitation. A yellow crystalline material, M.P.=74°–75° C., comprising dl-2-benzyloxy-6-azido-5,6,7,8-tetrahydro-1-naphthoic acid, was obtained.

Analysis Calculated: C, 66.86; H, 5.30; N, 13.00. Found: C, 66.63; H, 5.39; N, 12.79.

Mass spectrum: molecular ion at 323.

Six and fifty-six hundredths grams of the above acid were heated to reflux temperature overnight in 100 ml. of thionyl chloride. The reaction mixture was then cooled to room temperature and the volatile constituents removed in vacuo. The residue containing dl-2-benzyloxy-6-azido-5,6,7,8-tetrahydro-1-naphthoyl chloride was diluted with chloroform. About 100 ml. of 14N aqueous ammonium hydroxide were then added. This new reaction mixture was stirred for one hour at ambient temperature and was then diluted with water. The organic phase was separated and the aqueous phase extracted several times with equal volumes of chloroform. The chloroform phases were combined and the combined phases washed with water and with saturated aqueous sodium chloride and were then dried. Evaporation of the chloroform yielded a dark viscous oil. Trituration of the oil with $CHCl_3$ yielded a solid which was filtered and the filter cake dissolved in chloroform. The chloroform solution was chromatographed over 100 g. of florisil using chloroform containing increasing amounts (0–2%) of methanol as the eluant. One and eight tenths grams of a solid material were obtained showing a single spot ($R_f$=0.46) on TLC in ether; dl-2-benzyloxy-6-azido-5,6,7,8-tetrahydro-1-naphthalenecarboxamide thus prepared melted at 128°–130° C.

Analysis Calculated: C, 67.07; H, 5.63; N, 17.38. Found: C, 66.87; H, 5.52; N, 17.48.

Yield was 38.6%.

A solution was prepared by dissolving 0.7 g. of dl-2-benzyloxy-6-azido-5,6,7,8-tetrahydro-1-naphthalenecarboxamide in 50 ml. of ethanol. The solution was placed in a low pressure hydrogenation apparatus and hydrogenated over a palladium-on-carbon catalyst at about 60 psi. After the theoretical quantity of hydrogen had been absorbed, the hydrogenation mixture was removed from the apparatus and the catalyst separated by filtration. Evaporation of the solvent from the filtrate yielded dl-2-hydroxy-6-amino-5,6,7,8-tetrahydro-1-naphthalenecarboxamide. The residue was dissolved in methanol and gaseous hydrogen chloride passed into the methanol solution, thus forming the hydrochloride salt. Ether was added to the solution to the point of incipient precipitation and the solution was cooled. Crystalline dl-2-hydroxy-6-amino-5,6,7,8-tetrahydro-1-naphthalenecarboxamide hydrochloride thus obtained melted at 245° C.; yield=0.3 g.

Analysis Calculated: C, 54.44; H, 6.23; N, 11.54. Found: C, 54.57; H, 6.05; N, 11.36.

Mass spectrum: molecular ion at 296.

EXAMPLE 5

Alternate preparation of dl-2-Hydroxy-6-di-n-propylamino-5,6,7,8-tetrahydro-1-naphthalenecarboxamide A solution was prepared from 3.4 g. of dl-2-benzyloxy-6-azido-5,6,7,8-tetrahydro-1-naphthalenecarboxamide (from Example 4) and 100 ml. of isopropanol. The solution was cooled and 0.5 g. sodium borohydride added thereto in small portions. After the addition had been completed, the reaction mixture was heated to reflux temperature under a nitrogen blanket for about 18 hours. The reaction mixture was then cooled and the cooled mixture diluted with water. The aqueous mixture was made acidic by the addition of 1N aqueous hydrochloric acid. The aqueous acidic layer was extracted with ether and the ether extract discarded. The aqueous acidic layer was made basic by the addition of 10% aqueous sodium hydroxide. The alkaline layer was extracted several times with equal volumes of a 3:1 chloroform/methanol solvent mixture. The organic extracts were combined and the combined extracts washed with saturated aqueous sodium chloride and then dried. Evaporation of the solvent therefrom yielded a residue comprising dl-2-benzyloxy-6-amino-5,6,7,8-tetrahydro-1-naphthalenecarboxamide. TLC indicated a single spot at the origin. An infrared spectrum of the solid indicated no absorption attributable to an azide group. The residue was dissolved in chloroform and the chloroform solution saturated with gaseous hydrogen chloride. The solvent was removed in vacuo and the residue dissolved in methanol. Ether was added to the point of incipient precipitation and the solution was cooled overnight. Forty-eight hundredths grams of tan crystals melting above 235° C. consisting of dl-2-benzyloxy-6-amino-5,6,7,8-tetrahydro-1-naphthalenecarboxamide hydrochloride were recovered.

Analysis Calculated: C, 64.96; H, 6.36; N, 8.42. Found: C, 64.72; N, 6.54; N, 8.36.

Mass spectrum: molecular ion at 296.

Alternatively, 0.5 g of dl-2-benzyloxy-6-azido-5,6,7,8-tetrahydro-1-naphthalenecarboxamide were dissolved in 100 ml. of a 1:1 THF/ethanol solvent mixture. About 1 g. of Raney nickel were added and the mixture stirred at about 0° C. while 5 ml. of hydrazine hydrate were added thereto in dropwise fashion. After the addition had been completed, the reaction mixture was stirred for 4 hours at ambient temperature after which time it was filtered. The solvent was removed from the filtrate leaving a yellow residue. TLC indicated a single spot with $R_f$=0.63 using a 63:7:27:3 chloroform/methanol/acetone/ammonium hydroxide solvent system. Yield of dl-2-benzyloxy-6-amino-5,6,7,8-tetrahydro-1-naphthalenecarboxamide was 0.46 g. (100%). This 0.46 g. sample was alkylated with propionaldehyde and sodium cyanoborohydride by the procedure of Example 1 to yield dl-2-benzyloxy-6-di-n-propylamino-5,6,7,8-tetrahydro-1-naphthalenecarboxamide hydrochloride. TLC (9:1 chloroform/methanol) $R_f$=0.40.

Mass spectrum: molecular ion at 380.

Analysis Calculated: C, 69.13; H, 7.98; N, 6.72. Found: C, 69.00; H, 8.17; N, 6.50.

The benzyl group was removed by hydrogenation over a palladium-on-carbon catalyst according to the procedure of Example 1 to yield about 0.4 g. of dl-2-hydroxy-6-di-n-propylamino-5,6,7,8-tetrahydro-1-naphthalenecarboxamide hydrochloride.

The hydrochloride salt was converted back to the free base by standard procedures and the free base chromatographed. Fractions containing dl-2-hydroxy-6-di-n-propylamino-5,6,7,8-tetrahydro-1-naphthalenecarboxamide were combined and the solvent removed by evaporation. The solid was reconverted to the hydrochloride salt in ethanol with gaseous hydrogen chloride. Ether was added to the ethanol solution to the point of incipient precipitation and the solution cooled to about −15° C. Crystalline dl-2-hydroxy-6-di-n-propylamino-5,6,7,8-tetrahydro-1-naphthalenecarboxamide hydrochloride thus purified melted at 168°–170° C.; yield=29.4 mg.

Mass spectrum: molecular ion at 290.

Analysis Calculated: C, 62.47; H, 8.33; N, 8.57; Cl, 10.85. Found: C, 62.27; H, 8.04; N, 8.58; Cl, 11.06.

EXAMPLE 6

Alternate preparation of Methyl dl-2-Benzyloxy-6-amino-5,6,7,8-tetrahydro-1-naphthoate A solution was prepared from about 10 g. of methyl 2-benzyloxy-5-oxo-5,6,7,8-tetrahydro-1-napthoate in 250 ml. of methanol to which was added 10 g. of sodium borohydride in small portions with cooling. After the borohydride had been added, the mixture was stirred for about 3 hours and then diluted with water. The aqueous layer was extracted several times with equal volumes of chloroform. The chloroform extracts were combined and the combined extracts were washed with saturated aqueous sodium chloride and then dried. Evaporation of the solvent yielded 7.0 g. of an oil comprising methyl dl-2-benzyloxy-5-hydroxy-5,6,7,8-tetrahydro-1-naphthoate.

The oily residue was dissolved in 400 ml. of toluene to which were added 3 g. of Amberlite ®15 as a dehydrating agent. The mixture was distilled under a nitrogen blanket for about 15 minutes after which time it was filtered, and the filtrate cooled. The solvent was removed from the cooled filtrate by evaporation. The resulting residue was recrystallized from an ether/hexane solvent mixture to yield 6.5 g. of methyl 2-benzyloxy-7,8-dihydro-1-napthoate melting at 97°–100° C.

The above compound was also prepared by the following sequence of reactions: Methyl 2-benzyloxy-5-oxo-5,6,7,8-tetrahydro-1-naphthoate was brominated with pyridinium bromide perbromide in glacial acetic acid. Methyl dl-2-benzyloxy-5-oxo-6-bromo-5,6,7,8-tetrahydro-1-napthoate melting at 120°–4° C. was obtained. Twenty-six grams of the bromo ketone were suspended in 600 ml. of methanol and 20 g. of sodium borohydride added. Twenty-four and five tenths grams of methyl dl-2-benzyloxy-5-hydroxy-6-bromo-5,6,7,8-tetrahydro-1-naphthoate melting at 120°–2° C. were obtained. Thirty-one and three tenths grams of the hydroxybromo compound were mixed with 70 g. of zinc dust and 400 ml. of glacial acetic acid. The reaction mixture was heated at reflux temperature for about 3 hours under a nitrogen blanket and was then filtered. The filtrate was poured over ice and the aqueous mixture extracted with ethyl acetate. The ethyl acetate layer was separated and the separated layer washed with water, aqueous sodium bicarbonate, again with water, and finally with saturated aqueous sodium chloride. The organic layer was dried and the solvent was evaporated therefrom in vacuo. Seventeen and five tenths grams of methyl 2-benzyloxy-7,8-dihydro-1-naphthoate melting at 88°–92° C. were obtained by this route.

A reaction mixture was prepared from 6.5 g. of methyl 2-benzyloxy-7,8-dihydro-1-naphthoate, 4.8 g. of 85% m-chloroperbenzoic acid, 250 ml. of chloroform and 25 ml. of anhydrous ethanol. The reaction mixture was allowed to remain overnight at ambient temperature. Evaporation of the volatile constituents in vacuo left a residue which was dissolved in chloroform. The chloroform solution was filtered through about 150 g. of alumina (grade I). Two and three tenths grams of methyl dl-2-benzyloxy-5-ethoxy-6-hydroxy-5,6,7,8-tetrahydro-1-naphthoate melting at 133°–7° C. were obtained from the filtrate after crystallization from an ether-hexane solvent mixture.

Analysis calculated: C, 70.77; H, 6.79. Found: C, 70.72; H, 6.66.

Nine and six tenth grams of methyl dl-2-benzyloxy-5-ethoxy-6-hydroxy-5,6,7,8-tetrahydro-1-naphthoate were mixed with 4 g. of Amberlite ®15 and 250 ml. of toluene. The mixture was heated to refluxing temperature for about 15 minutes and was then filtered and the filtrate cooled. Evaporation of the filtrate to dryness yielded a residue which was dissolved in 300 ml. of methanol to which was added 23 g. of ammonium acetate. Ten grams of sodium cyanoborohydride were added thereto in portions. The reaction mixture was stirred at ambient temperature under a nitrogen blanket overnight. It was then diluted with 1N aqueous hydrochloric acid and the acidic layer extracted with ether. The ether extract was discarded. The aqueous layer was made basic with 14N ammonium hydroxide and the alkaline layer extracted several times with equal volumes of chloroform. The chloroform extracts were combined and the combined extracts washed with saturated aqueous sodium chloride and then dried. Evaporation of the chloroform in vacuo yielded a residue comprising methyl dl-2-benzyloxy-6-amino-5,6,7,8-tetrahydro-1-naphthoate. The free base was dissolved in ethanol and converted to the hydrochloride salt by the addition of 2 ml. of 12N aqueous hydrochloric acid. One and twenty-five hundredths grams of hydrochloride salt were obtained. The hydrochloride salt was converted to the free base by standard procedures. Sixty-four hundredths grams of free base thus obtained were dissolved in boiling methanol to which was added 280 mg. of oxalic acid dihydrate. Six hundred milligrams of the oxalate salt of methyl dl-2-benzoxy-6-amino-5,6,7,8-tetrahydro-1-naphthoate melting at 181°–3° C. were obtained.

Analysis calculated: C, 62.84; H, 5.78; N, 3.49. Found: C, 62.64; H, 5.79; N, 3.44.

The primary amine thus prepared can be debenzylated by hydrogenation over a palladium-on-carbon catalyst and the resulting compound converted to the carboxamide by procedures set forth in the above examples. Alternatively, the amine can be alkylated with formaldehyde, acetaldehyde or propionaldehyde in the presence of sodium cyanoborohydride and the resulting dialkylamine debenzylated and the free-hydroxy compound converted to the carboxamide also by procedures of the above examples.

EXAMPLE 7

Preparation of dl-3-Hydroxy-7-amino-5,6,7,8-tetrahydro-2-naphthlenecarboxamide Twenty-four and eight tenths grams of methyl 3-benzyloxy-8-oxo-5,6,7,8-tetrahydro-2-naphthoate were dissolved in a mixture of 200 ml. of THF and 200 ml. of methanol. Twenty-eight grams of pyridinium perbromide hydrobromide were added and the reaction mixture stirred at ambient temperature for 2.5 hours after which time it was diluted with water and the resulting aqueous mixture extracted with chloroform. The chloroform extract containing methyl dl-3-benzyloxy-7-bromo-8-oxo-5,6,7,8-tetrahydro-2-naphthoate was washed with saturated aqueous sodium chloride and then dried. The solvent was removed therefrom by evaporation. The resulting residue was dissolved in 500 ml. of DMF containing 10 ml. of glacial acetic acid. The solution was cooled in an ice-water bath to about 0° C. A solution of 12 g. of sodium azide in 100 ml. of water was added. The reaction mixture was cooled for 2 hours, and was then diluted with water. The aqueous mixture extracted with ethyl acetate. The ethyl acetate extract was washed with water and with saturated aqueous sodium chloride and was then dried. Evaporation of the ethyl acetate yielded a residue comprising methyl dl-3-benzyloxy-7-azido-8-oxo-5,6,7,8-tetrahydro-2-naphthoate. The residue was dissolved in THF and the THF solution diluted with 400 ml. of methanol. The solution was cooled to about 0° C. and 20 g. of sodium borohydride added thereto in portions. The reaction mixture was stirred at ambient temperature for about 2 hours and was then diluted with water, and the resulting aqueous mixture extracted with chloroform. The chloroform layer was separated; the separated layer washed with water and with saturated aqueous sodium chloride and then dried. Evaporation of the chloroform yielded methyl dl-3-benzyloxy-7-azido-8-hydroxy-5,6,7,8-tetrahydro-2-naphthoate. This residue was chromatographed over 400 g. of florisil using hexane containing increasing amounts (0–100%) ether as the eluant. Twenty grams of the hydroxy azide were obtained from fractions shown by TLC to contain the desired material.

About 20 g. of methyl dl-3-benzyloxy-7-azido-8-hydroxy-5,6,7,8-tetrahydro-2-naphthoate thus obtained were dissolved in 150 ml. of carbon tetrachloride to which was added 25 g. of triethylsilane and 30 ml. of trifluoroacetic acid. The reaction mixture was stirred for about 20 minutes at room temperature and was then poured over ice. The aqueous mixture was made basic with 14N ammonium hydroxide. The alkaline layer was extracted with chloroform. The chloroform extract was separated and the separated extract washed with saturated aqueous sodium chloride and then dried. Evaporation of the chloroform yielded methyl dl-3-benzyloxy-7-azido-5,6,7,8-tetrahydro-2-naphthoate. The residue was dissolved in 250 ml. of THF and 250 ml. of methanol. Ten grams of Raney nickel were added to this mixture followed by the dropwise addition of 10 ml. of 85% hydrazine hydrate in 40 ml. of methanol. This reaction mixture was stirred for about 30 minutes and then filtered. The filtrate was concentrated in vacuo and the concentrated filtrate diluted with ethyl acetate. The ethyl acetate layer was extracted several times with 10% aqueous hydrochloric acid. The aqueous layer and acidic extracts were then made basic with 14N ammonium hydroxide and the basic layer extracted with chloroform. The chloroform extract was separated and the separated extract washed with saturated aqueous sodium chloride and then dried. Evaporation of the solvent yielded 15.5 g. of methyl dl-3-benzyloxy-7-amino-5,6,7,8-tetrahydro-2-naphthoate.

A portion of the above free base was converted to the hydrochloride salt. Eight and nine tenths grams of this salt were dissolved in methanol containing 1 ml. of water. Two grams of 5% palladium-on-carbon were added and the mixture hydrogenated at 60 psi. The hydrogenation mixture was then filtered and the filtrate evaporated to dryness in vacuo. A white solid shown by TLC to consist of a single spot comprising methyl dl-3-hydroxy-7-amino-5,6,7,8-tetrahydro-2-naphthoate hydrochloride was obtained. This white solid was dissolved in methanol and the methanol solution cooled to about 0° C. The cooled solution was saturated with gaseous ammonia and the resulting mixture allowed to remain at ambient temperature for about 17 days. At this time, TLC indicated the amidation reaction had gone substantially to completion. The reaction mixture was decolorized with carbon and filtered and the filtrate concentrated in vacuo to yield about 3.5 g. of dl-3-hydroxy-7-amino-5,6,7,8-tetrahydro-2-naphthalenecarboxamide hydrochloride melting at about 300° C.

Analysis Calculated: C, 54.44; H, 6.23; N, 11.54; Cl, 14.61. Found: C, 54.17; H, 6.07; N, 11.30; Cl, 14.45.

As previously stated, the compounds of this invention are dopamine agonists. As such, one of their properties, shared by many dopamine agonists, is the ability to lower blood pressure in anesthetized spontaneously hypertensive rats (SHR). Table 1 which follows gives the results of testing compounds of this invention which lowered the blood pressure of anesthetized SHR at dose levels of 1 mg./kg. or lower. In the Table, the first 4 columns give the substitution pattern of the hydroxyaminonaphthalene carboxamide and the second 4 columns the percent blood pressure lowering±standard error for the particular compound at 4 different dose levels.

TABLE 1

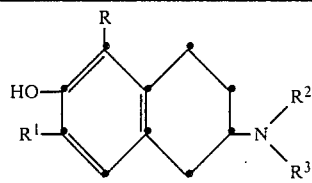

Percent lowering of mean arterial blood pressure anesthetized spontaneously hypertensive rats

| Substitution Pattern | | | | Dose | | | |
| --- | --- | --- | --- | --- | --- | --- | --- |
| R | $R^1$ | $R^2$ | $R^3$ | 7 mcg./kg. | 10 mcg./kg. | 100 mcg./kg. | 1 mg./kg. |
| H | $CONH_2$ | H | H | $-3.6 \pm 0.4$ | $-5.2 \pm 0.8$ | $-10.2 \pm 1.2$ | $-18.3 \pm 4.3$ |
| H | " | Me | Me | $-6.2 \pm 0.7$ | $-14.0 \pm 0.5$ | $-25.1 \pm 3.0$ | $-32.5 \pm 2.2$ |
| H | " | n-Pr | n-Pr | $-6.8 \pm 0.5$ | $-19.6 \pm 0.8$ | $-35.9 \pm 2.3$ | $-41.9 \pm 1.6$ |
| $CONH_2$ | H | Me | Me | $-6.8 \pm 0.3$ | $-5.7 \pm 0.3$ | $-6.7 \pm 0.8$ | $-6.0 \pm 0.5$ |

Compounds with dopaminergic or dopamine agonist activity also affect turning behavior in a test procedure utilizing 6-hydroxydopamine-lesioned rats. In this test, nigro-neostriatal-lesioned rats, prepared by the procedure of Ungerstedt and Arbuthnott, Brain Res, 24, 485 (1970), are employed. A compound having dopamine agonist activity, upon injection, causes the rats to turn in circles contralateral to the side of the lesion. After a latency period, which varies from compound to compound, the number of turns is counted over a 15-minute period. The drugs to be administered are dissolved in water and the resulting aqueous solution injected into the rat by the intraperitoneal route at a 1 mg./kg. dose level. Table 2 which follows gives the results of such tests. In Table 2, column 1 gives the name of the compound, column 2 the percent of rats exhibiting turning behavior and column 3 the average number of turns.

TABLE 2
Turning Behavior

| Name of Compound | Percentage of rats exhibiting turning behavior | Number of turns |
| --- | --- | --- |
| dl-3-hydroxy-7-dimethylamino-5,6,7,8-tetrahydronaphthalene-2-carboxamide | 50 | 20 |
| dl-3-hydroxy-7-di-n-propylamino-5,6,7,8-tetrahydronaphthalene-2-carboxamide | 75 | 71 |

The compounds of this invention are also useful as inhibitors of prolactin secretion. Dopaminergic drugs with such activity can be employed in the treatment of inappropriate lactation, such as postpartum lactation and galactorrhea. The compounds of this invention have been shown to inhibit prolactin secretion according to the following procedure: Adult male rats of the Sprague-Dawley strain weighing about 200 g. were housed in an air-conditioned room with controlled lighting (lights on 6 a.m.–8 p.m.) and fed lab chow and water ad libitum. Each rat received an intraperitoneal injection of 2.0 mg. of reserpine in aqueous suspension 18 hours before administration of the test compound. The purpose of the reserpine was to keep prolactin levels uniformly elevated. The compounds under test were dissolved in water and were injected intraperitoneally at a 1 mg./kg. dose level. Each compound was administered to a group of 10 rats, and a control group of 10 intact males received an equivalent amount of solvent only. One hour after treatment all rats were killed by decapitation, and 150 µl. aliquots of serum were assayed for prolactin.

The results of this prolactin secretion inhibition test are given in Table 3 below. In the table, column 1 gives the name of the compound and column 2, the percent inhibition of prolactin secretion. The dosage was 1 mg./kg.

TABLE 3
Prolactin Secretion Inhibition

| Name of Compound | Percent Inhibition of Prolactin Secretion with Confidence Level |
| --- | --- |
| dl-3-hydroxy-7-di-n-propylamino-5,6,7,8-tetrahydronaphthalene-2-carboxamide | 88 ($p < 0.01$) |
| dl-3-hydroxy-7-dimethylamino-5,6,7,8-tetrahydronaphthalene-2-carboxamide | 36 ($p < 0.05$) |
| dl-2-hydroxy-6-amino-5,6,7,8-tetrahydronaphthalene-1-carboxamide | 13 (N.S.) |
| dl-3-hydroxy-7-amino-5,6,7,8-tetrahydronaphthalene-2-carboxamide | 18 (N.S.) |
| dl-2-hydroxy-6-di-n-propylamino-5,6,7,8-tetrahydronaphthalene-1-carboxamide | 12 (N.S.) |

In using the dopaminergic compounds of this invention to inhibit prolactin secretion or to treat Parkinson's syndrome or as hypotensive drugs or for other dopaminergic pharmacologic action, a compound according to Formula I, above, or a salt thereof with a pharmaceutically-acceptable acid, is administered to a subject suffering from Parkinsonism or hypertension, or needing to have his or her prolactin level reduced, in an amount effective to alleviate some of the symptoms of Parkinsonism or to reduce blood pressure or to reduce an elevated prolactin level. Oral administration is preferred. If parenteral administration is used, administration is preferably by the subcutaneous route using an appropriate pharmaceutical formulation. Other modes of parenteral administration such as intraperitoneal, intramuscular, or intravenous routes are equally effective. In particular, with intravenous or intramuscular administration, a water soluble pharmaceutically-acceptable salt is employed. For oral administration, a compound according to Formula I either as the free base or in the form of a salt thereof, is mixed with standard pharmaceutical excipients and the mixture loaded into empty telescoping gelatin capsules or pressed into tablets. The oral dosage should be in the range 0.01–10 mg./kg. of mammalian body weight and the parenteral dose in the range 0.0025 to 2.5 mg./kg.

We claim:

1. A method for reducing elevated blood pressure in a mammal having high blood pressure and in need of treatment which comprises administering to said mammal a hypotensive dose of a drug of the formula

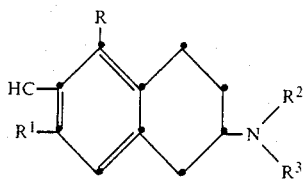

wherein one of R and R¹ is H and the other is $CONH_2$, R² and R³ are individually H, methyl, ethyl or n-propyl, and a pharmaceutically-acceptable acid addition salt thereof formed with a non-toxic acid.

2. A process according to claim 1 in which dl-3-hydroxy-7-di-n-propylamino-5,6,7,8-tetrahydro-2-naphthalenecarboxamide is the drug administered.

3. A process according to claim 1 in which dl-3-hydroxy-7-dimethylamino-5,6,7,8-tetrahydro-2-naphthalenecarboxamide is the drug administered.

4. A method of inhibiting the secretion of prolactin in mammals which comprises administering to a mammal having a condition accompanied by excess prolactin secretion and in need of treatment a prolactin secretion inhibiting dose of a drug of the formula

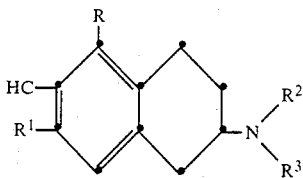

wherein one of R and R¹ is H and the other is $CONH_2$, R² and R³ are individually H, methyl, ethyl or n-propyl, and a pharmaceutically-acceptable acid addition salt thereof formed with a non-toxic acid.

5. A process according to claim 4 in which dl-3-hydroxy-7-di-n-propylamino-5,6,7,8-tetrahydro-2-naphthalenecarboxamide is the drug administered.

6. A process according to claim 4 in which dl-3-hydroxy-7-dimethylamino-5,6,7,8-tetrahydro-2-naphthalenecarboxamide is the drug administered.

7. A method of treating Parkinson's Syndrome which comprises administering to a human suffering from Parkinson's Syndrome and in need of treatment, a dose of a drug of the formula

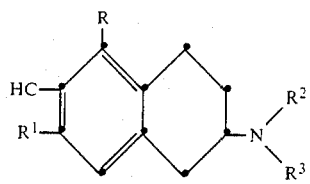

wherein one of R and R¹ is H and the other is $CONH_2$, R² and R³ are individually H, methyl, ethyl or n-propyl, and a pharmaceutically-acceptable acid addition salts thereof formed with a non-toxic acid effective to alleviate some or all of the manifestations of Parkinson's Syndrome.

8. A process according to claim 7 in which dl-3-hydroxy-7-di-n-propylamino-5,6,7,8-tetrahydro-2-naphthalenecarboxamide is the drug administered.

9. A process according to claim 7 in which dl-3-hydroxy-7-dimethylamino-5,6,7,8-tetrahydro-2-naphthalenecarboxamide is the drug administered.

10. A pharmaceutical formulation in unit dosage form adapted for administration to achieve a dopaminergic effect containing per unit dosage a dopaminergically-effective amount of a drug of the formula U.S. Ser. No. 588,180

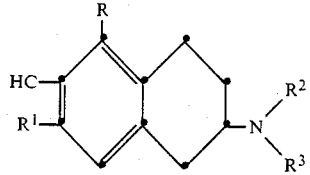

wherein one of R and R¹ is H and the other is $CONH_2$, R² and R³ are individually H, methyl, ethyl or n-propyl, and a pharmaceutically-acceptable acid addition salt thereof formed with a non-toxic acid plus one or more pharmaceutical excipients.

11. A formulation according to claim 10 in which dl-3-hydroxy-7-di-n-propylamino-5,6,7,8-tetrahydro-2-naphthalenecarboxamide is the active drug.

12. A formulation according to claim 10 in which dl-3-hydroxy-7-dimethylamino-5,6,7,8-tetrahydro-2-naphthalenecarboxamide is the active drug.

* * * * *

UNITED STATES PATENT AND TRADEMARK OFFICE
CERTIFICATE OF CORRECTION

PATENT NO. : 4,500,545

DATED : February 19, 1985

INVENTOR(S) : Nicholas J. Bach et al.

It is certified that error appears in the above—identified patent and that said Letters Patent is hereby corrected as shown below:

Columns 33 and 34, lines 5-10 and 30-35, that portion of the formula which reads:

"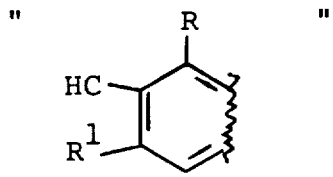"

should read:

-- 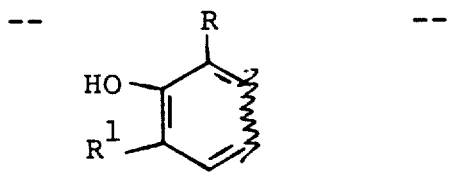 --

Column 34, lines 27 and 28, delete "U.S. Ser. No. 588,180".

Signed and Sealed this

Twenty-fifth Day of March 1986

[SEAL]

Attest:

DONALD J. QUIGG

Attesting Officer

Commissioner of Patents and Trademarks